(12) United States Patent
Klepač

(10) Patent No.: US 9,801,735 B2
(45) Date of Patent: Oct. 31, 2017

(54) MODULAR SURGICAL TOOL ASSEMBLY

(71) Applicant: Gary W. Klepač, Austin, TX (US)

(72) Inventor: Gary W. Klepač, Austin, TX (US)

(73) Assignee: Renovis Surgical Technologies, Inc., Redlands, CA (US)

( * ) Notice: Subject to any disclaimer, the term of this patent is extended or adjusted under 35 U.S.C. 154(b) by 14 days.

(21) Appl. No.: 14/806,978

(22) Filed: Jul. 23, 2015

(65) Prior Publication Data
US 2016/0022342 A1 Jan. 28, 2016

Related U.S. Application Data

(60) Provisional application No. 62/028,063, filed on Jul. 23, 2014.

(51) Int. Cl.
*A61B 17/00* (2006.01)
*A61F 2/46* (2006.01)
*A61B 90/00* (2016.01)
A61B 17/16 (2006.01)
A61F 2/44 (2006.01)
A61F 2/30 (2006.01)

(52) U.S. Cl.
CPC ............ *A61F 2/4684* (2013.01); *A61B 90/06* (2016.02); *A61B 17/1659* (2013.01); *A61B 17/1671* (2013.01); *A61B 2090/061* (2016.02); *A61F 2/4455* (2013.01); *A61F 2002/30471* (2013.01); *A61F 2002/4623* (2013.01); *A61F 2002/4658* (2013.01)

(58) Field of Classification Search
CPC ................................ A61F 2/44; A61F 2/4684
See application file for complete search history.

(56) References Cited

U.S. PATENT DOCUMENTS

| | | | | |
|---|---|---|---|---|
| 8,187,334 B2 * | 5/2012 | Curran | .................... | A61F 2/447 623/17.16 |
| 8,435,296 B2 * | 5/2013 | Kadaba | .................... | A61F 2/44 623/17.12 |
| 9,445,918 B1 * | 9/2016 | Lin | .................... | A61B 17/8819 |
| 2004/0143332 A1 * | 7/2004 | Krueger | ............... | A61B 17/025 623/17.14 |
| 2007/0123985 A1 * | 5/2007 | Errico | .................. | A61B 17/025 623/17.11 |
| 2008/0077153 A1 * | 3/2008 | Pernsteiner | ........... | A61F 2/4425 606/99 |
| 2008/0109005 A1 * | 5/2008 | Trudeau | ................ | A61F 2/4425 606/99 |
| 2009/0057168 A1 * | 3/2009 | Smit | .................. | A61B 17/8833 206/221 |
| 2009/0182343 A1 * | 7/2009 | Trudeau | ................ | A61F 2/4657 606/102 |
| 2012/0143204 A1 * | 6/2012 | Blaylock | ............... | A61F 2/3859 606/99 |

(Continued)

*Primary Examiner* — Ellen C Hammond
*Assistant Examiner* — Stuart S Bray
(74) *Attorney, Agent, or Firm* — Clements Bernard Walker PLLC; Christopher L. Bernard

(57) ABSTRACT

A modular surgical tool that is used to insert instruments into the intervertebral disc space of a patient to measure the height of the intervertebral disc space, to prepare the intervertebral disc space for an implant, and to insert the implant into the intervertebral disc space using a plurality of interchangeable tool ends. Advantageously, this modular surgical tool permits multiple insertion angles.

18 Claims, 10 Drawing Sheets

(56) References Cited

U.S. PATENT DOCUMENTS

| | | | | |
|---|---|---|---|---|
| 2012/0232659 | A1* | 9/2012 | Himmelberger | A61F 2/44 623/17.16 |
| 2012/0265303 | A1* | 10/2012 | Refai | A61F 2/44 623/17.11 |
| 2013/0150858 | A1* | 6/2013 | Primiano | A61B 17/16 606/80 |
| 2013/0261629 | A1* | 10/2013 | Anthony | A61B 17/16 606/80 |
| 2013/0325019 | A1* | 12/2013 | Thomas | A61B 17/157 606/88 |
| 2014/0012383 | A1* | 1/2014 | Triplett | A61F 2/4425 623/17.16 |
| 2014/0121774 | A1* | 5/2014 | Glerum | A61F 2/4611 623/17.16 |
| 2014/0135776 | A1* | 5/2014 | Huffmaster | A61F 2/4684 606/90 |
| 2014/0277472 | A1* | 9/2014 | Gray | A61F 2/442 623/17.15 |
| 2014/0336652 | A1* | 11/2014 | Christensen | A61F 2/4425 606/79 |
| 2015/0018957 | A1* | 1/2015 | Nichols | A61F 2/4611 623/17.16 |
| 2015/0202053 | A1* | 7/2015 | Willis | A61F 2/44 606/86 A |
| 2015/0297247 | A1* | 10/2015 | Seex | A61F 2/4684 623/17.11 |
| 2016/0235448 | A1* | 8/2016 | Seex | A61B 17/1728 |
| 2016/0242923 | A1* | 8/2016 | Davenport | A61F 2/442 |
| 2016/0242934 | A1* | 8/2016 | van der Walt | A61F 2/4684 |

\* cited by examiner

MODULAR SURGICAL TOOL ASSEMBLY

CROSS-REFERENCE TO RELATED APPLICATION

The present patent application/patent claims the benefit of priority of U.S. Provisional Patent Application No. 62/028,063, filed on Jul. 23, 2014, and entitled "MODULAR SURGICAL TOOL," the contents of which are incorporated in full by reference herein.

FIELD OF THE INVENTION

The present invention relates generally to a modular surgical tool. More specifically, the present invention relates to a modular surgical tool that is used to insert instruments into the intervertebral disc space of a patient to measure the height of the intervertebral disc space, to prepare the intervertebral disc space for an implant, and to insert the implant into the intervertebral disc space using a plurality of interchangeable tool ends. Advantageously, this modular surgical tool permits multiple insertion angles.

BACKGROUND OF THE INVENTION

A variety of conventional surgical tools exist for measuring the height of the intervertebral disc space of a patient, preparing the intervertebral disc space for an implant, and inserting the implant into the intervertebral disc space. However, no single conventional surgical tool exists for performing all of these functions sequentially and efficiently, and no conventional surgical tool exists that allows a surgeon to take advantage of multiple insertion angles with an easy adjustment mechanism. The present invention provides such a surgical tool.

BRIEF SUMMARY OF THE INVENTION

In various exemplary embodiments, the present invention provides a modular surgical tool that is used to insert instruments into the intervertebral disc space of a patient to measure the height of the intervertebral disc space, to prepare the intervertebral disc space for an implant, and to insert the implant into the intervertebral disc space using a plurality of interchangeable tool ends. Advantageously, this modular surgical tool permits multiple insertion angles.

In one exemplary embodiment, the present invention provides a modular surgical tool assembly, comprising: an elongate shaft assembly; a handle assembly coupled a proximal end of the elongate shaft assembly; a tool end attachment assembly coupled to a distal end of the elongate shaft assembly; and a tool end assembly coupled to the tool end attachment assembly; wherein the tool end attachment assembly is configured to selectively allow the tool end assembly to be pivoted with respect to the elongate shaft assembly. The tool end attachment assembly comprises a boss that is disposed within a corresponding recess manufactured into the tool end assembly. The tool end assembly comprises one of a spacer assembly, a broach assembly, a retention assembly, and a manipulation assembly. The modular surgical tool assembly further comprises a handle attachment assembly disposed between the handle assembly and the elongate shaft assembly. The handle attachment assembly further comprises a shoulder stop disposed between the handle assembly and the elongate shaft assembly. The modular surgical tool assembly further comprises an axially aligned post structure protruding from the distal end of the elongate shaft assembly. The tool end attachment assembly is disposed at least partially concentrically about the axially aligned post structure. The modular surgical tool assembly further comprises a spring member disposed at least partially concentrically about the axially aligned post structure between the tool end attachment assembly and a should stop associated with the elongate shaft assembly. Optionally, the handle assembly is configured to selectively rotate with respect to the elongate shaft assembly. Optionally, the tool end attachment assembly is configured to selectively rotate with respect to the elongate shaft assembly.

In another exemplary embodiment, the present invention provides a method for providing a modular surgical tool assembly, comprising: providing an elongate shaft assembly; providing a handle assembly coupled a proximal end of the elongate shaft assembly; providing a tool end attachment assembly coupled to a distal end of the elongate shaft assembly; and providing a tool end assembly coupled to the tool end attachment assembly; wherein the tool end attachment assembly is configured to selectively allow the tool end assembly to be pivoted with respect to the elongate shaft assembly. The tool end attachment assembly comprises a boss that is disposed within a corresponding recess manufactured into the tool end assembly. The tool end assembly comprises one of a spacer assembly, a broach assembly, a retention assembly, and a manipulation assembly. The method for providing the modular surgical tool assembly further comprises providing a handle attachment assembly disposed between the handle assembly and the elongate shaft assembly. The handle attachment assembly further comprises a shoulder stop disposed between the handle assembly and the elongate shaft assembly. The method for providing the modular surgical tool assembly further comprises providing an axially aligned post structure protruding from the distal end of the elongate shaft assembly. The tool end attachment assembly is disposed at least partially concentrically about the axially aligned post structure. The method for providing the modular surgical tool assembly further comprises providing a spring member disposed at least partially concentrically about the axially aligned post structure between the tool end attachment assembly and a should stop associated with the elongate shaft assembly. Optionally, the handle assembly is configured to selectively rotate with respect to the elongate shaft assembly. Optionally, the tool end attachment assembly is configured to selectively rotate with respect to the elongate shaft assembly.

BRIEF DESCRIPTION OF THE DRAWINGS

The present invention is illustrated and described herein with reference to the various drawings, in which like reference numbers are used to denote like assembly components/method steps, as appropriate, and in which.

DETAILED DESCRIPTION OF THE INVENTION

Again, in various exemplary embodiments, the present invention provides a modular surgical tool that is used to insert instruments into the intervertebral disc space of a patient to measure the height of the intervertebral disc space, to prepare the intervertebral disc space for an implant, and to insert the implant into the intervertebral disc space using a plurality of interchangeable tool ends. Advantageously, this modular surgical tool permits multiple insertion angles.

Figure 1:
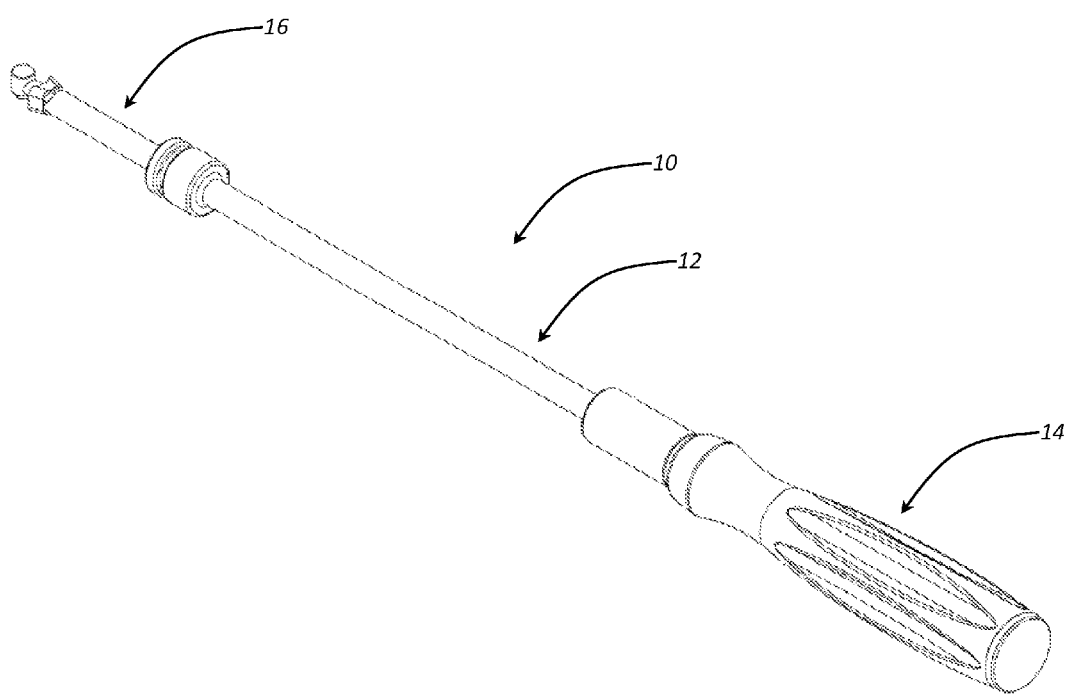
FIG. 1 is a perspective view of one exemplary embodiment of the modular surgical tool assembly of the present invention.

Referring now specifically to FIG. 1, in one exemplary embodiment, the modular surgical tool assembly 10 of the present invention includes an elongate shaft assembly 12, a handle assembly 14, and a tool end attachment assembly 16. Advantageously, these various components allow desired amounts of rotation and/or pivotal movement of a tool end assembly with respect to the elongate shaft assembly 12 and/or handle assembly 14. The various components also allow interchangeable tool ends to be used.

Figure 2:
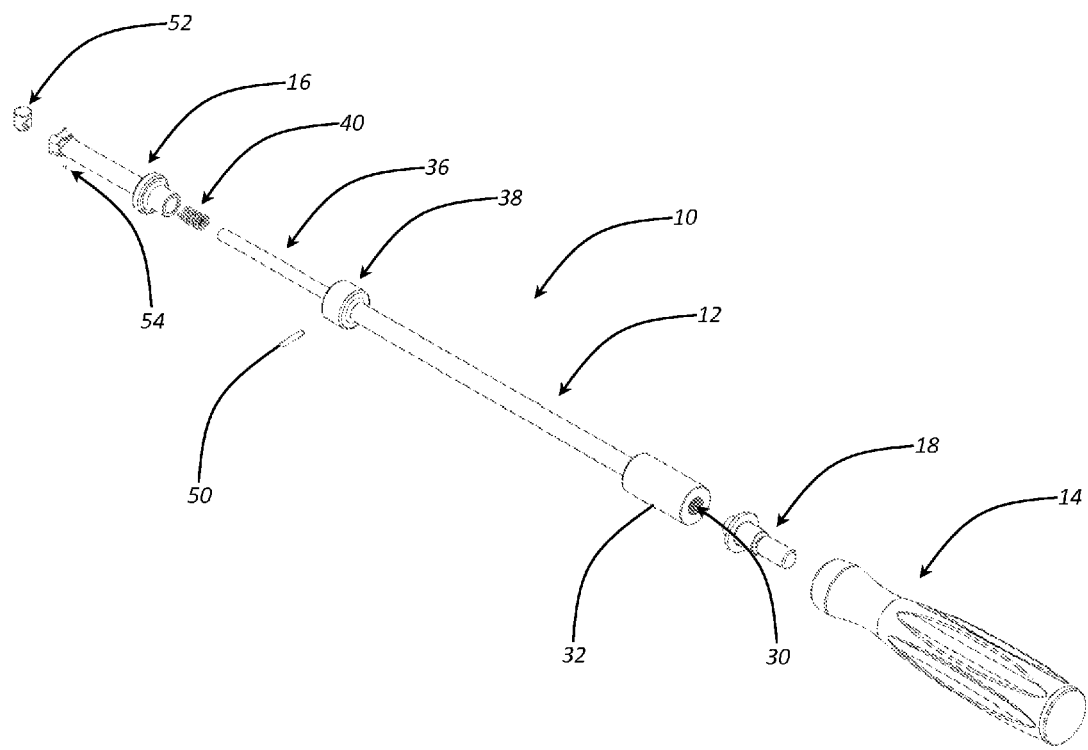
FIG. 2 is an exploded perspective view of one exemplary embodiment of the modular surgical tool assembly of the present invention.
Figure 3:
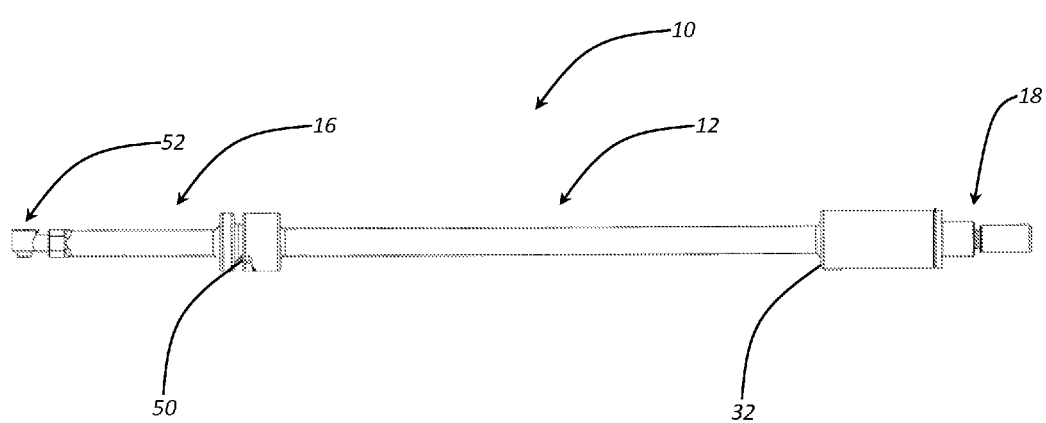
FIG. 3 is a planar view of one exemplary embodiment of the modular surgical tool assembly of the present invention.
Figure 4:
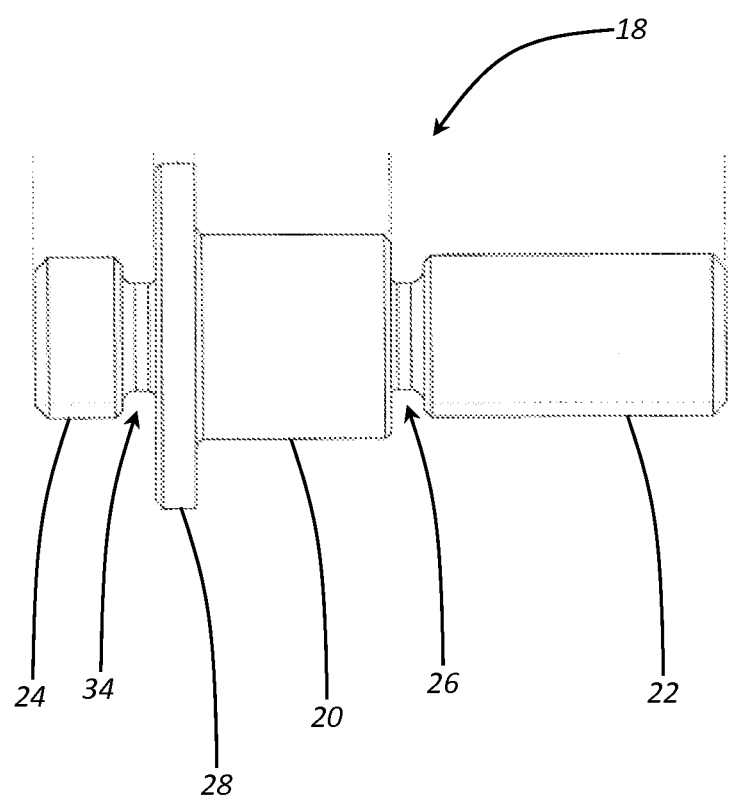
FIG. 4 is a planar view of one exemplary embodiment of the handle attachment assembly of the modular surgical tool assembly of the present invention.

Referring now specifically to FIG. 2, the handle assembly 14 is selectively coupled to the elongate shaft assembly 12 via a handle attachment assembly 18. This handle attachment assembly 18 is shown coupled to the elongate shaft assembly in FIG. 3 and is shown in greater detail in FIG. 4. The handle attachment assembly 18 includes a central bore portion 20 that is coupled to a first protruding portion 22 on a proximal end thereof and a second protruding portion 24 on a distal end thereof. The first protruding portion 22 is configured to mate with a corresponding recess or bore manufactured in an end of the handle assembly 14. Accordingly, the first protruding portion 22 may be chamfered or otherwise form a recess 26 adjacent to the central bore portion 20. This recess 26 selectively engages a lip structure, bearing, or the like manufactured into or disposed within the recess or bore manufactured into the end of the handle assembly 14, thereby allowing the handle attachment assembly 18 to be "snapped" or otherwise press-fit into the handle assembly 14 in a removable and/or rotatable manner. Alternatively, a threaded or other attachment mechanism may be utilized. Optionally, all or a portion of the central bore portion 20 is disposed within the handle assembly 14 when the handle attachment assembly 18 is engaged with the handle assembly 14. A shoulder stop 28 is provided to limit the depth of penetration of the handle attachment assembly 18 into the handle assembly 14. The second protruding portion 24 is configured to mate with a corresponding recess or bore 30 manufactured in an end of the elongate shaft assembly 12. In this exemplary embodiment, the recess or bore 30 is manufactured into a widened portion 32 of the elongate shaft assembly 12. Accordingly, the second protruding portion 24 may be chamfered or otherwise form a recess 34 adjacent to the central bore portion 20. This recess 34 selectively engages a lip structure, bearing, or the like manufactured into or disposed within the recess or bore 30 manufactured into the end of the elongate shaft assembly 12, thereby allowing the handle attachment assembly 18 to be "snapped" or otherwise press-fit into the elongate shaft assembly 12 in a removable and/or rotatable manner. Alternatively, a threaded or other attachment mechanism may be utilized. Again, a shoulder stop 28 is provided to limit the depth of penetration of the handle attachment assembly 18 into the elongate shaft assembly 12.

Figure 5:
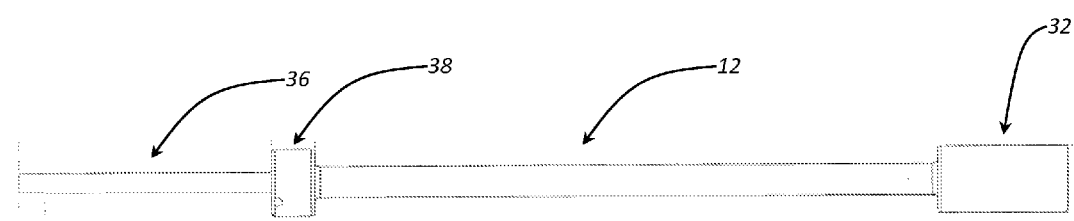
FIG. 5 is a planar view of one exemplary embodiment of the elongate shaft assembly of the modular surgical tool assembly of the present invention.
Figure 6:
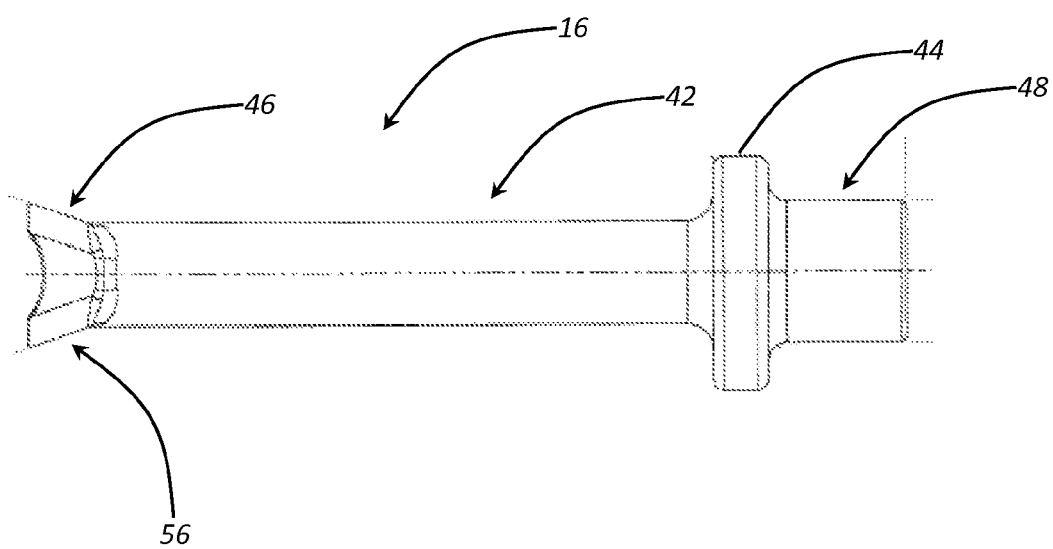
FIG. 6 is a planar view of one exemplary embodiment of the tool end attachment assembly of the modular surgical tool assembly of the present invention.

Referring now specifically to FIGS. 2 and 5, at the opposite end of the elongate shaft assembly 12, an axially aligned post portion 36 and shoulder stop 38 are provided. The tool end attachment assembly 16 is disposed concentrically about the axially aligned post portion 36 and essentially mates with the shoulder stop 38. A spring member 40 or the like is disposed between the tool end attachment assembly 16 and the shoulder stop 38, about the axially aligned post portion 36. This arrangement provides the tool end attachment assembly 16 with a desired degree of rotational and/or translational movement with respect to the elongate shaft assembly 12, and provides a damping effect for the tool end ultimately attached to the tool end attachment assembly 16. As shown in FIG. 6, the tool end attachment assembly 16 includes a hollow tube 42 that terminates in a shoulder stop 44 at a proximal end thereof and tool end connector 46 at a distal end thereof. A hollow bore portion 48 is disposed at the proximal end of the hollow tube 42, opposite the hollow tube 42 with respect to the shoulder stop 44. In this exemplary embodiment, the hollow bore portion 48 is disposed with a recess or bore manufactured into an end of the shoulder stop 38 of the elongate shaft assembly 12, opposite the handle assembly 14. The hollow bore portion 48 is disposed concentrically about the axially aligned post portion 36 and the spring member 40. The hollow bore portion 48 may selectively retained in the shoulder stop 38 of the elongate shaft assembly 12 using any of a variety of mechanisms, such as a pin 50 that is disposed through the shoulder stop 38 and into a recess or channel manufactured into the exterior of the hollow bore portion 48, etc. The tool end connector 46 is a fan shaped structure that selectively receives a fixed or pivotal boss member 52, that is optionally connected to the tool end connector via a pivot pin 54, etc. The tool end connector 46 includes side walls 56 or the like that limit or bound the motion of the boss member 52 within the tool end connector 46, when such motion is allowed. Any other type and/or number of mechanisms, such as detents or the like, may also be used to selectively grade and retain the motion of the boss member 52 within the tool end connector 46, when such motion is allowed.

Figure 7:
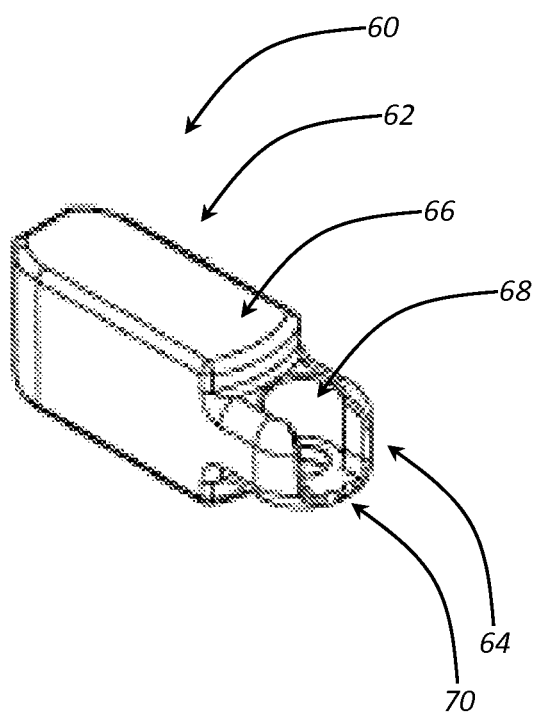
FIG. 7 is a perspective view of one exemplary embodiment of a tool end assembly of the modular surgical tool assembly of the present invention, the tool end assembly for measuring intervertebral disc space height.
Figure 8:
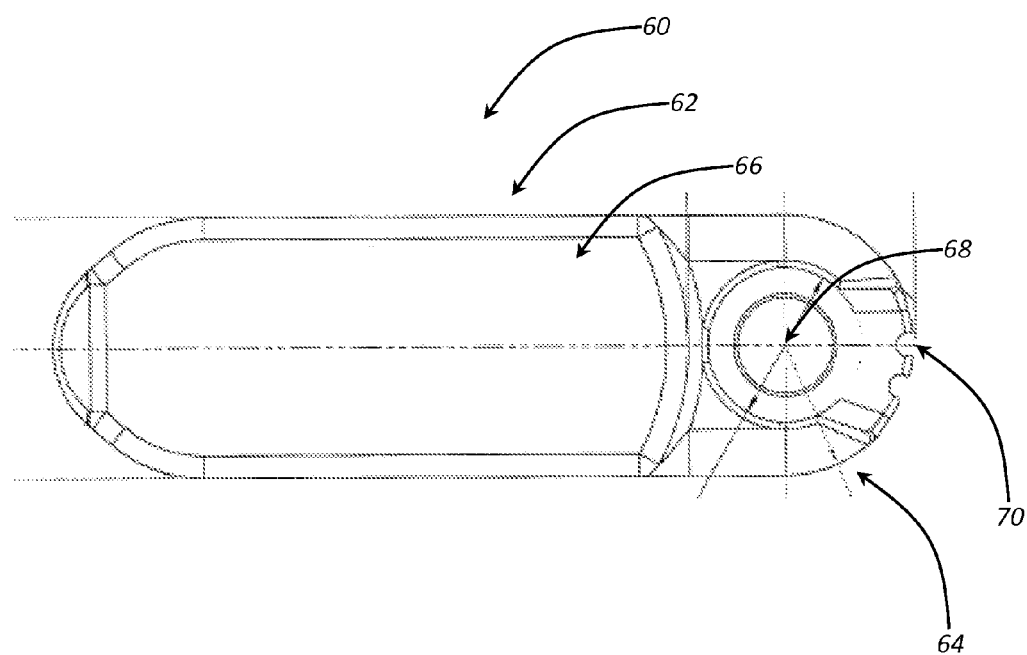
FIG. 8 is a planar view of one exemplary embodiment of a tool end assembly of the modular surgical tool assembly of the present invention, the tool end assembly for measuring intervertebral disc space height.

Referring now specifically to FIGS. 7 and 8, in one exemplary embodiment, the tool end assembly 60 of the present invention is a height (i.e. intervertebral space) measurement device and includes a head portion 62 and an attachment portion 64. The head portion 62 includes opposed, parallel smooth surfaces 66 that enable the head portion to be inserted into the intervertebral space, thereby indicating its height, distracting it, etc. The attachment portion 64 includes a recess 68 that substantially conforms to the boss 52 of the tool end attachment assembly 16, such that the tool end assembly 60 and the tool end attachment assembly 16 are selectively coupled together in a selected (fixed or changeable) pivotal orientation. Optionally, a plurality of detents 70 are provided for this purpose.

Figure 9:
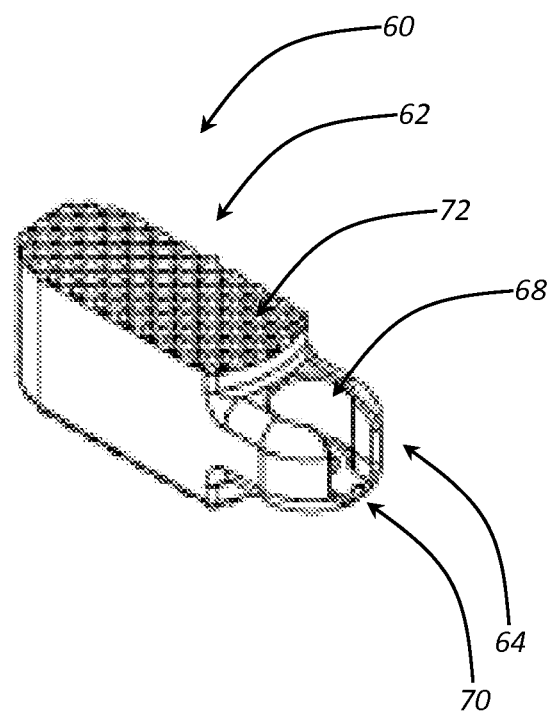
FIG. 9 is a perspective view of another exemplary embodiment of a tool end assembly of the modular surgical tool assembly of the present invention, the tool end assembly for shaping the intervertebral disc space.
Figure 10:
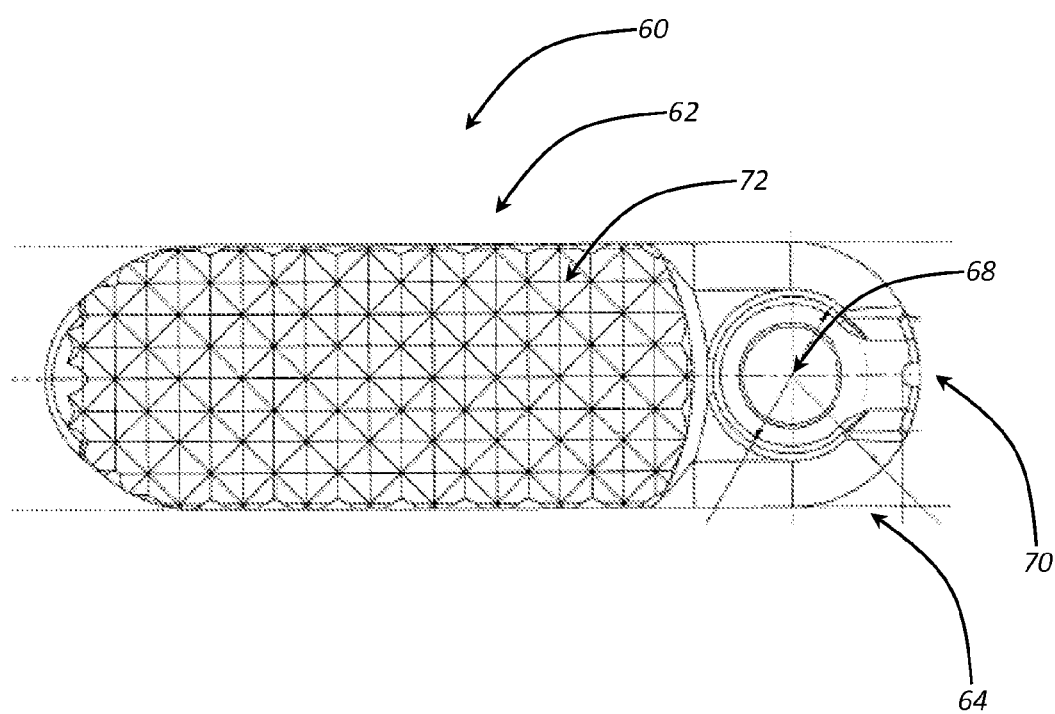
FIG. 10 is a planar view of another exemplary embodiment of a tool end assembly of the modular surgical tool assembly of the present invention, the tool end assembly for shaping the intervertebral disc space.

Referring now specifically to FIGS. 9 and 10, in another exemplary embodiment, the tool end assembly 60 of the present invention is an intervertebral space preparation device and includes a head portion 62 and an attachment portion 64. The head portion 62 includes opposed, parallel rasp surfaces 72 that enable the head portion to be inserted into the intervertebral space to prepare the endplates for later implant insertion and bony purchase, etc. The attachment portion 64 includes a recess 68 that substantially conforms to the boss 52 of the tool end attachment assembly 16, such that the tool end assembly 60 and the tool end attachment assembly 16 are selectively coupled together in a selected (fixed or changeable) pivotal orientation. Optionally, a plurality of detents 70 are provided for this purpose.

It will be readily apparent to those of ordinary skill in the art that the tool end of the present invention may also be any conventional tool, such as a spacer, rasp, grasping tool, manipulation tool, etc. Further, as a general note, all components of the present invention may be sized, shaped, and manufactured from materials as is conventional for surgical tools.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A modular surgical tool assembly, comprising:
   an elongate shaft assembly;
   a handle assembly coupled to a proximal end of the elongate shaft assembly;
   a tool end attachment assembly coupled to a distal end of the elongate shaft assembly; and
   a tool end assembly coupled to the tool end attachment assembly;
   wherein the tool end attachment assembly comprises a boss that is disposed within a corresponding recess manufactured into the tool end assembly; and
   wherein the boss is a separate component that is pivotally attached within and pivots within the tool end attachment assembly and the tool end assembly pivots about the boss.

2. The modular surgical tool assembly of claim 1, wherein the tool end assembly comprises one of a spacer assembly, a broach assembly, a retention assembly, and a manipulation assembly.

3. The modular surgical tool assembly of claim 1, further comprising a handle attachment assembly disposed between the handle assembly and the elongate shaft assembly.

4. The modular surgical tool assembly of claim 3, wherein the handle attachment assembly further comprises a shoulder stop disposed between the handle assembly and the elongate shaft assembly.

5. The modular surgical tool assembly of claim 1, further comprising an axially aligned post structure protruding from the distal end of the elongate shaft assembly.

6. The modular surgical tool assembly of claim 5, wherein the tool end attachment assembly is disposed at least partially concentrically about the axially aligned post structure.

7. The modular surgical tool assembly of claim 5, further comprising a spring member disposed at least partially concentrically about the axially aligned post structure between the tool end attachment assembly and a shoulder stop associated with the elongate shaft assembly.

8. The modular surgical tool assembly of claim 1, wherein the handle assembly is configured to selectively rotate with respect to the elongate shaft assembly.

9. The modular surgical tool assembly of claim 1, wherein the tool end attachment assembly is configured to selectively rotate with respect to the elongate shaft assembly.

10. A method for providing a modular surgical tool assembly, comprising:
    providing an elongate shaft assembly;
    providing a handle assembly coupled to a proximal end of the elongate shaft assembly;
    providing a tool end attachment assembly coupled to a distal end of the elongate shaft assembly; and
    providing a tool end assembly coupled to the tool end attachment assembly;
    wherein the tool end attachment assembly comprises a boss that is disposed within a corresponding recess manufactured into the tool end assembly; and
    wherein the boss is a separate component that is pivotally attached within and pivots within the tool end attachment assembly and the tool end assembly pivots about the boss.

11. The method for providing the modular surgical tool assembly of claim 10, wherein the tool end assembly comprises one of a spacer assembly, a broach assembly, a retention assembly, and a manipulation assembly.

12. The method for providing the modular surgical tool assembly of claim 10, further comprising providing a handle attachment assembly disposed between the handle assembly and the elongate shaft assembly.

13. The method for providing the modular surgical tool assembly of claim 12, wherein the handle attachment assembly further comprises a shoulder stop disposed between the handle assembly and the elongate shaft assembly.

14. The method for providing the modular surgical tool assembly of claim 10, further comprising providing an axially aligned post structure protruding from the distal end of the elongate shaft assembly.

15. The method for providing the modular surgical tool assembly of claim 14, wherein the tool end attachment assembly is disposed at least partially concentrically about the axially aligned post structure.

16. The method for providing the modular surgical tool assembly of claim 14, further comprising providing a spring member disposed at least partially concentrically about the axially aligned post structure between the tool end attachment assembly and a shoulder stop associated with the elongate shaft assembly.

17. The method for providing the modular surgical tool assembly of claim 10, wherein the handle assembly is configured to selectively rotate with respect to the elongate shaft assembly.

18. The method for providing the modular surgical tool assembly of claim 10, wherein the tool end attachment assembly is configured to selectively rotate with respect to the elongate shaft assembly.

* * * * *